(12) United States Patent
Wagberg et al.

(10) Patent No.: US 9,695,194 B2
(45) Date of Patent: Jul. 4, 2017

(54) BENZOXAZINONE DERIVATIVES FOR TREATMENT OF SKIN DISEASES

(71) Applicant: SIXERA PHARMA AB, Gothenburg (SE)

(72) Inventors: Fredrik Wagberg, Lerum (SE); Goran Leonardsson, Kungsbacka (SE)

(73) Assignee: SIXERA PHARMA AB (SE)

( * ) Notice: Subject to any disclaimer, the term of this patent is extended or adjusted under 35 U.S.C. 154(b) by 0 days.

(21) Appl. No.: 15/113,750

(22) PCT Filed: Jan. 22, 2015

(86) PCT No.: PCT/SE2015/050062
§ 371 (c)(1),
(2) Date: Jul. 22, 2016

(87) PCT Pub. No.: WO2015/112081
PCT Pub. Date: Jul. 30, 2015

(65) Prior Publication Data
US 2017/0002021 A1  Jan. 5, 2017

(30) Foreign Application Priority Data
Jan. 23, 2014  (SE) ...................................... 1430003

(51) Int. Cl.
*C07D 498/04* (2006.01)
*A61K 31/536* (2006.01)
*C07D 265/22* (2006.01)

(52) U.S. Cl.
CPC .......... *C07D 498/04* (2013.01); *A61K 31/536* (2013.01); *C07D 265/22* (2013.01)

(58) Field of Classification Search
CPC ................................................ C07D 498/04
USPC ......................................................... 544/92
See application file for complete search history.

(56) References Cited

U.S. PATENT DOCUMENTS

| 7,872,052 B2 | 1/2011 | Linschoten |
| 2006/0258651 A1 | 11/2006 | Linschoten |

FOREIGN PATENT DOCUMENTS

| GB | 1 153 994 A | 6/1969 |
| WO | 99/48878 A1 | 9/1999 |
| WO | 2004/108139 A2 | 12/2004 |

OTHER PUBLICATIONS

International Search Report issued in International Application No. PCT/SE2015/050062 with Date of mailing May 5, 2015.
Written Opinion of the International Searching Authority issued in International Application No. PCT/SE2015/050062 with Date of mailing May 5, 2015.
Torbjorn Egelrud, "Purification and preliminary characterization of stratum corneum chymotryptic enzyme: a proteinase that may be involved in desquamation," J. Invest. Dermatol., 1993, vol. 101, pp. 200-204.
Skytt et al., "Primary substrate specificity of recombinant human stratum corneum chymotryptic enzyme," Biochemical and Biophysical Research Communications, Jun. 15, 1995, vol. 211, No. 2, pp. 586-589.
Yousef et al. "The KLK7 (PRSS6) gene, encoding for the stratum corneum chymotryptic enzyme is a new member of the human kallikrein gene family—genomic characterization, mapping, tissue expression and hormonal regulation," 2000, Gene 254, pp. 119-1281.
Simon et al., "Refined characterization of comeodesmosin proteolysis during terminal differentiation of human epidermis and its relationship to desquamation," The Journal of Biological Chemistry, Issue of Jun. 8, 2001, vol. 276, No. 23, pp. 20292-20299.
Caubet et al., "Degradation of comeodesmosome proteins by two serine proteases of the kallikrein family, SCTE/KLK5/hK5 and SCCE/KLK7/hK7," J. Invest. Dermatol., 2004, vol. 122, pp. 1235-1244.
Brattsand et al., "A proteolytic cascade of kallikreins in the stratum corneum," J. Invest. Dermatol., 2005, vol. 124, pp. 198-203.
Hachem et al., "Sustained serine proteases activity by prolonged increase in pH leads to degradation of lipid processing enzymes and profound alterations of barrier function and stratum corneum integrity," J. Invest. Dermatol., 2005, vol. 125, pp. 510-520.
Nylander-Lundqvist & Egelrud, "Formation of active IL-1/3f om pro-IL-113 catalyzed by stratum corneum chymotryptic enzyme in vitro," Acta Derm. Venereol (Stockh), 1997, vol. 77, pp. 203-206.
Vasilopoulos et al., "Genetic association between an AACC insertion in the 3'UTR of the stratum corneum chymotryptic enzyme gene and atopic dermatitis," J. Invest. Dermatol., 2004, vol. 123, pp. 62-66.
Schechter et al., "Inhibition of human kallikreins 5 and 7 by the serine protease inhibitor lympho-epithelial Kazal-type inhibitor (LEKTI)," Biol. Chem., Nov. 2005, vol. 386, pp. 1173-1184.
Franzke et al., "Antileukoprotease inhibits stratum corneum chymotryptic enzyme—Evidence for a regulative function in desquamation," The Journal of Biological Chemistry, Issue of Sep. 6, 1996, vol. 271, No. 36, pp. 21886-21890.
Descargues et al., "Spink5-deficient mice mimic Netherton syndrome through degradation of desmoglein 1 by epidermal protease hyperactivity," Nature Genetics, Jan. 2005, vol. 37, No. 1, pp. 56-65.
Walley et al., "Gene polymorphism in Netherton and common atopic disease," Nature Genetics, Oct. 2001, vol. 29, pp. 175-178.
Nishio et al., "Association between polymorphisms in the SPINK5 gene and atopic dermatitis in the Japanese," Genes Immunity, (2003), vol. 4, pp. 515-517.

(Continued)

*Primary Examiner* — Kahsay Habte
(74) *Attorney, Agent, or Firm* — Eric L. Sophir; Dentons US LLP

(57) ABSTRACT

The present invention relates to methods and compositions for inhibiting the activity of skin proteases, especially human kallikrein 7 (KLK7), human kallikrein 5 (KLK5), and human kallikrein 14 (KLK14). More specifically, the invention relates to the use of substituted 3,1-benzoxazin-4-ones being selective inhibitors of human skin kallikreins for the treatment of skin diseases, more specifically for the treatment of inflammatory skins diseases, especially Netherton syndrome.

5 Claims, No Drawings

(56) References Cited

OTHER PUBLICATIONS

Descargues et al., "Corneodesmosomal cadherins are preferential targets of stratum corneum trypsin- and chymotrypsin-like hyperactivity in Netherton syndrome," Journal of Investigative Dermatology, (2006), vol. 126, pp. 1622-1632.

Hachem et al., "Serine protease activity and residual LEKTI expression determine phenotype in Netherton syndrome," Journal of Investigative Dermatology, (2006), vol. 126, pp. 1609-1621.

Hansson et al., "Epidermal Overexpression of Stratum Corneum Chymotryptic Enzyme in Mice: A Model for Chronic Itchy Dermatitis," Journal of Investigative Dermatology, 2002, vol. 118, pp. 444-449.

Ny & Egelrud, "Transgenic mice over-expressing a serine protease in the skin: evidence of interferon gamma-independent MHC II expression by epidermal keratinocytes," Acta Derm. Venereol, 2004, vol. 84, pp. 322-327.

Ny & Egelrud, "Epidermal hyperproliferation and decreased skin barrier function in mice overexpressing stratum corneum chymotryptic enzyme," Acta Derm. Venereol, 2004, vol. 84, pp. 18-22.

Ekholm & Egelrud, "Stratum corneum chymotryptic enzyme in psoriasis," Arch. Dermatol. Res., (1999), vol. 291, pp. 195-200.

BENZOXAZINONE DERIVATIVES FOR TREATMENT OF SKIN DISEASES

CROSS-REFERENCE TO RELATED APPLICATIONS

This application is a National Stage Entry of International Application No. PCT/SE2015/050062, filed on Jan. 22, 2015, and claims the benefit of and priority to SE 1430003-2, filed Jan. 23, 2014, which are hereby incorporated by reference into this application in their entirety.

FIELD OF THE INVENTION

The present invention relates to methods and compositions for inhibiting the activity of skin proteases, especially human kallikrein 7 (KLK7), human kallikrein 5 (KLK5), and human kallikrein 14 (KLK14). More specifically, the invention relates to the use of substituted 3,1-benzoxazin-4-ones being selective inhibitors of human skin kallikreins for the treatment of skin diseases, more specifically for the treatment of inflammatory skin diseases, especially Netherton syndrome.

BACKGROUND

KLK7 (hK7, or stratum corneum chymotryptic enzyme (SCCE), Swissprot P49862) is a S1 serine protease of the kallikrein gene family displaying a chymotrypsin like activity. KLK7 is mainly expressed in the skin and appears to play an important role in skin physiology (Egelrud. 1993. *Purification and preliminary characterization of stratum corneum chymotryptic enzyme: a proteinase that may be involved in desquamation. J. Invest. Dermatol.* 101, 200-204; Skytt et al. 1995. *Primary substrate specificity of recombinant human stratum corneum chymotryptic enzyme. Biochem Biophys Res Commun* 211, 586-589; Yousef et al. 2000. *The KLK7 (PRSS6) gene, encoding for the stratum corneum chymotryptic enzyme is a new member of the human kallikrein gene family—genomic characterization, mapping, tissue expression and hormonal regulation. Gene* 254, 119-1281).

KLK7 is involved in the degradation of the intercellular cohesive structure in cornified squamous epithelia in the process of desquamation. The desquamation process is well regulated and delicately balanced with the de novo production of corneocytes to maintain a constant thickness of the stratum corneum. In this regard, KLK7 is reported to be able to cleave the corneodesmosomal proteins comeodesmosin and desmocollin 1 (Simon et al. 2001. *Refined characterization of comeodesmosin proteolysis during terminal differentiation of human epidermis and its relationship to desquamation. J. Biol. Chem.* 276, 20292-20299; Caubet et al. 2004. *Degradation of corneodesmosome proteins by two serine proteases of the kallikrein family, SCTE/KLK5/hK5 and SCCE/KLK7/hK7. J. Invest. Dermatol.* 122, 1235-1244; Brattsand et al. 2005. *A proteolytic cascade of kallikreins in the stratum corneum. J. Invest. Dermatol.* 124, 198-203. In addition, it has been shown that the two lipid processing enzymes β-glucocerebrosidase and acidic sphingomyelinase can be degraded by KLK7 (Hachem et al. 2005. *Sustained serine proteases activity by prolonged increase in pH leads to degradation of lipid processing enzymes and profound alterations of barrier function and stratum corneum integrity. J. Invest. Dermatol.* 125, 510-520). Both lipid processing enzymes are co-secreted with their substrates glucosylceramides and sphingomyelin and process these polar lipid precursors into their more non-polar products e.g. ceramides, which are subsequently incorporated into the extracellular lamellar membranes. The lamellar membrane architecture is critical for a functional skin barrier. Finally, KLK7 has been shown to activate the pro-inflammatory cytokine Pro-interleukin-1β (IL-1(3) (Nylander-Lundqvist & Egelrud. 1997. *Formation of active IL-1β from pro-IL-1β catalyzed by stratum corneum chymotryptic enzyme in vitro. Acta Derm. Venereol.* 77, 203-206).

Several studies link an increased activity of KLK7 to inflammatory skin diseases like atopic dermatitis, psoriasis or Netherton syndrome. An increased KLK7 activity might lead to an uncontrolled degradation of corneodesmosomes resulting in a miss-regulated desquamation, an enhanced degradation of lipid processing enzymes resulting in a disturbed lamellar membrane architecture or an uncontrolled (in)activation of the pro-inflammatory cytokine IL-1β. It has previously been demonstrated that this could lead to an impaired skin barrier function and inflammation (WO 2004/108139).

The KLK7 activity is controlled on several levels. Various factors might be responsible for an increased KLK7 activity in inflammatory skin diseases. Firstly, the amount of protease being expressed might be influenced by genetic factors. Such a genetic link, a polymorphism in the 3'-UTR in the KLK7 gene, was recently described (Vasilopoulos et al. 2004. *Genetic association between an AACC insertion in the 3'UTR of the stratum corneum chymotryptic enzyme gene and atopic dermatitis. J. Invest. Dermatol.* 123, 62-66.). The authors hypothesis that the described 4 base pair insertion in the 3'-UTR of the kallikrein 7 gene stabilizes the KLK7 mRNA and results in an overexpression of KLK7. Secondly, since KLK7 is secreted via lamellar bodies to the stratum corneum extracellular space as zymogen and it is not able to autoactivate, it needs to be activated by another protease e.g. KLK5 (Caubet et al. supra). Uncontrolled activity of such an activating enzyme might result in an over activation of KLK7. Thirdly, activated KLK7 can be inhibited by natural inhibitors like LEKTI, ALP or elafin (Schechter et al. 2005. *Inhibition of human kallikreins 5 and 7 by the serine protease inhibitor lympho-epithelial Kazal-type inhibitor (LEKTI). Biol. Chem.* 386, 1173-1184; Franzke et al. 1996. *Antileukoprotease inhibits stratum corneum chymohyptic enzyme—Evidence for a regulative function in desquamation. J. Biol. Chem.* 271, 21886-21890). The decreased expression or the lack of such inhibitors might result in an enhanced activity of KLK7.

It has been found that mutations in the spink gene, coding for LEKTI, are causative for Netherton syndrome (Descargues et al. 2005. *Spink5—deficient mice mimic Netherton syndrome through degradation of desmoglein 1 by epidermal protease hyperactivity. Nat. Genet.* 37, 56-65) and a single point mutation in the gene is linked to atopic dermatitis (Walley et al. 2001. *Gene polymorphism in Netherton and common atopic disease. Nat. Genet.* 29, 175-178; Nishio et al. 2003. *Association between polymorphisms in the SPINK5 gene and atopic dermatitis in the Japanese. Genes Immun.* 4, 515-517). Finally, another level of controlling the activity of KLK7 is the pH. KLK7 has a neutral to slightly alkaline pH optimum and there is a pH gradient from neutral to acidic from the innermost to the outermost layers in the skin. Environmental factors like soap might result in a pH increase in the outermost layers of the stratum corneum towards the pH optimum of KLK7 thereby increasing the KLK7 activity.

The hypothesis that an increased activity of KLK7 is linked to inflammatory skin diseases is supported by the following studies: Firstly, Netherton syndrome patients show a phenotype dependent increase in serine protease activity, a decrease in corneodesmosomes, a decrease in the lipid processing enzymes β-glucocerebrosidase and acidic sphingomyelinase, and an impaired barrier function (Descargues et al. 2006. *Corneodesmosomal cadherins are preferential targets of stratum corneum trypsin-and chymotrypsin-like hyperactivity in Netherton syndrome. J. Invest. Dermatol.* 126, 1622-1632; Hachem et al. 2006. *Serine protease activity and residual LEKTI expression determine phenotype in Netherton syndrome. J. Invest. Dermatol.* 126, 1609-1621.). Secondly, a transgenic mice overexpressing KLK7 shows a skin phenotype similar to that found in patients with atopic dermatitis (Hansson et al. 2002. *Epidermal Overexpression of Stratum Corneum Chymotryptic Enzyme in Mice: A Model for Chronic Itchy Dermatitis. J. Invest. Dermatol.* 118, 444-449; Ny & Egelrud. 2003. *Transgenic mice over-expressing a serine protease in the skin: evidence of interferon gamma-independent MHC II expression by epidermal keratinocytes. Acta Derm. Venereol.* 83, 322-327; Ny & Egelrud. 2004. *Epidermal hyperproliferation and decreased skin barrier function in mice overexpressing stratum corneum chymotryptic enzyme. Acta Derm. Venereol.* 84, 18-22). Thirdly, in the skin of atopic dermatitis and psoriasis patients elevated levels of KLK7 were described (Elcholm & Egelrud. 1999. *Stratum corneum chymotryptic enzyme in psoriasis. Arch. Dermatol. Res.* 291, 195-200). Therefore, KLK7 is considered to be a target for the treatment of inflammatory skin diseases like atopic dermatitis, psoriasis or Netherton syndrome and there is a need for specific inhibitors thereof.

As patients suffering from Netherton syndrome have a severely impaired skin barrier, also topical administration of therapeutically active compounds will result in systemic exposure of the compounds to the patient. Accordingly, there is a need to identify inhibitors selective for skin proteases which can be used in the treatment of Netherton syndrome without risking systemic effects through unwanted systemic inhibition of proteases.

KLK7, KLK5, and KLK14 are believed to be part of a proteolytic cascade in the stratum corneum layer of human skin (Brattsand et al. 2005. *A proteolytic cascade of kallikreins in the stratum corneum. J Invest Dermatol* 124, 198-203).

Accordingly, it would be beneficial to identify inhibitors active not only on KLK7, but also on KLK5 and KLK14.

WO 2004/108139 describes certain substituted benzoxazinone and thienoxazinone compounds as inhibitors of KLK7, but fails to report any selectivity data for the described compounds.

DESCRIPTION OF THE INVENTION

The present inventors have been able to identify inhibitors being selective for skin protease and have found that the activity of KLK7, KLK5, and KLK14 can be selectively inhibited by compounds according to Formula I,

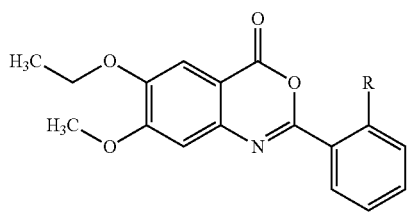

wherein R is S—CH₃ or —Cl.

Said compounds exhibit several advantageous properties, such as selectivity for the skin proteases KLK7, KLK5, and KLK14, involved in the pathophysiology of inflammatory skin diseases such as Netherton syndrome, having no or only low inhibitory activity on other proteases.

Accordingly, the present invention provides compounds according to Formula I

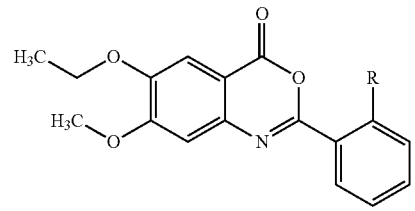 [SMILES: CCOc1cc2c(=O)oc(-c3ccccc3Cl)nc2cc1OC]

Formula I wherein R is —S—CH₃ or —Cl, or a pharmaceutically acceptable salt thereof The present invention further provides compounds according to Formula I or a pharmaceutical acceptable salt thereof, for use in in medicine.

The compound can be 6-Ethoxy-7-methoxy-2-(2-methylsulfanylphenyl)-3,1-benzoxazin-4-one, or 2-(2-Chlorophenyl)-6-ethoxy-7-methoxy-3,1-benzoxazin-4-one The present invention further provides compounds according to Formula I or a pharmaceutical acceptable salt thereof, for use in the prophylaxis, prevention and/or treatment of a skin disease.

The invention further provides pharmaceutical compositions comprising a compound according to Formula I in admixture with pharmaceutically acceptable adjuvants, diluents and/or carriers.

The invention further provides a pharmaceutical composition according to the invention for use in prophylaxis, prevention and/or treatment of a skin disease.

The invention further relates to the use of a compound according to the Formula I or a pharmaceutically acceptable salt thereof, for the manufacture of a medicament for the treatment of a skin disease.

The present invention further provides a method for the prophylaxis, prevention and/or treatment of a skin disease which comprises the administration of a therapeutically active amount of a compound according to Formula I or a pharmaceutical acceptable salt thereof, to a subject in need of such treatment.

The skin disease may be an inflammatory skin disease. The skin disease can be selected from Netherton syndrome, atopic dermatitis, contact dermatitis, eczema, psoriasis, acne, epidermal hyperkeratosis, acanthosis, epidermal inflammation, dermal inflammation and pruritus. The subject to be treated can be a mammal, such as a human, a dog, a cat, or a horse.

Definitions

As used herein, the term "pharmaceutically acceptable salts" includes acid addition salts and base addition salts. Such salts may be formed by conventional means, for example by reaction of a free acid or a free base form of the compound of the invention with one or more equivalents of an appropriate acid or base, optionally in a solvent, or in a medium in which the salt is insoluble, followed by removal of said solvent, or said medium, using standard techniques (e.g. in vacuo or by freeze-drying). Salts may also be prepared by exchanging a counter-ion of a compound of the invention in the form of a salt with another counter-ion using a suitable ion exchange resin.

In the context of the present specification, the term "treat" also includes "prophylaxis" unless there are specific indications to the contrary. The term "treat" within the context of the present invention further encompasses to administer an effective amount of a compound of the present invention, to mitigate either a pre-existing disease state, acute or chronic, or a recurring condition. This definition also encompasses prophylactic therapies for prevention of recurring condition and continued therapy for chronic disorders.

The compound of the present invention may be administered in the form of a conventional pharmaceutical composition by any route including orally, intramuscularly, subcutaneously, topically, intranasally, intraperitoneally, intrathoracially, intravenously, epidurally, intrathecally, intracerebroventricularly and by injection into the joints.

In one embodiment of the present invention, the route of administration may be topical.

The dosage will depend on the route of administration, the severity of the disease, age and weight of the patient and other factors normally considered by the attending physician, when determining the individual regimen and dosage level at the most appropriate for a particular patient.

For preparing pharmaceutical compositions from the compound of the present invention, inert, pharmaceutically acceptable carriers can be either solid or liquid. Solid form preparations include powders, tablets, dispersable granules, capsules, cachets, and suppositories.

A solid carrier can be one or more substances, which may also act as diluents, flavouring agents, solubilizers, lubricants, suspending agents, binders, or tablet disintegrating agents; it can also be an encapsulating material.

In powders, the carrier is a finely divided solid, which is in mixture with the finely divided compound of the present invention, or the active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogenous mixture is then poured into conveniently sized molds and allowed to cool and solidify.

Suitable carriers are magnesium carbonate, magnesium stearate, talc, lactose, sugar, pectin, dextrin, starch, methyl cellulose, sodium carboxymethyl cellulose, a low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavouring agents, stabilizers, and thickening agents as desired. Aqueous solutions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Depending on the mode of administration, the pharmaceutical composition will according to one embodiment of the present invention include 0.05% to 99% weight (percent by weight), according to an alternative embodiment from 0.10 to 50% weight, of the compound of the present invention, all percentages by weight being based on total composition.

A therapeutically effective amount for the practice of the present invention may be determined, by the use of known criteria including the age, weight and response of the individual patient, and interpreted within the context of the disease which is being treated or which is being prevented, by one of ordinary skills in the art.

The above-mentioned subject-matter for a pharmaceutical composition comprising a compound according to the present invention is applied analogously for a pharmaceutical composition comprising a combination according to the present invention.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

EXAMPLES

Example 1

Selectivity of substituted 3,1-benzoxazin-4-ones as inhibitors of human proteases $IC_{50}$ values for a number of substituted 3,1-benzoxazin-4-ones on a panel of human proteases were determined.

KLK7 Assay

Materials: Recombinant human KLK7, Substrate S-2586 (Chromogenics, cat. no. 820894) KLK7 activity was determined at 37° C. in 10 mM Na phosphate pH 7.2, 0.5 M NaCl, with final concentrations of 2.5 µg/ml (100 nM) of KLK7, 1.0 mM substrate, 5% DMSO in the presence of 0 µM, 0.1 µM, 0.5 µM, 1.0 µM and 5 µM of inhibitor, in 96 well plates by measuring absorbance at 405 nm in a plate reader (Spectramax).

KLK5 Assay

Materials: Recombinant human KLK5, Substrate S-2288 (Chromogenics, cat. no. 820852) KLK5 activity was determined at 37° C. in 0.1 M Tris, pH 8.0, 0.15 M NaCl, with final concentrations of 2.5 µg/ml KLK5, 1 mM substrate, 5% DMSO in the presence of 0 µM, 0.1 µM, 1.0 µM and 10 µM of inhibitor, in 96 well plates by measuring absorbance at 405 nm in a plate reader (Spectramax).

KLK14 Assay

Materials: Recombinant human KLK14, Substrate S-2302 (Chromogenics, cat. no. 820340). KLK14 activity was determined at 37° C. in 0.1 mM Tris, pH 8.0, 0.15 M NaCl, with final concentrations of 0.26 µg/ml (9.4 nM) of KLK14, 0.75 mM substrate, 5% DMSO, in the presence of 0 µM, 0.1 µM, 1.0 µM and 10 µM of inhibitor, in 96 well plates by measuring absorbance at 405 nm in a plate reader (Spectramax).

Cathepsin G Assay

Materials: Cathepsin G, 100 mU (VWR, Calbiochem, cat. no. 219373), Substrate Cathepsin G substrate (VWR, Calbiochem, cat. no. 219407)

Cathepsin activity was determined at 37° C. in 10 mM Na phosphate pH 7.2, 0.5 M NaCl, with final concentrations of 1.5 mU/ml (0.75 µg/ml, 32 nM) of Cathepsin G, 0.75 mM substrate, 5% DMSO, in the presence of 0 µM, 0.1 µM, 1.0 µM and 10 µM of inhibitor, in 96 well plates by measuring absorbance at 405 nm in a plate reader (Spectramax).

Chymotrypsin Assay

Materials: Chymotrypsin, bovine, 25 µg (Roche, sequence grade), Substrate S-2586 (Chromogenics, cat. no. 82 08 94)

Chymotrypsin activity was determined at 37° C. in 10 mM Na phosphate pH 7.2, 0.5M NaCl, with final concentrations of 0.2 µg/ml (6.8 nM) of Chymotrypsin, 1 mM substrate, 5% DMSO in the presence of 0 µM, 0.1 µM, 1.0 µM and 10 µM of inhibitor, in 96 well plates by measuring absorbance at 405 nm in a plate reader (Spectramax).

Trypsin Assay

Materials: Trypsin, 100 µg (Roche, sequence grade, Mw 23500), Substrate S-2288 (Chromogenics, cat. no. 820852)

Trypsin activity was determined at 37° C. in 10 mM Na phosphate pH 7.2, 0.5 M NaCl, with final concentrations of 0.8 µg/ml (34 nM) of Trypsin, 1 mM substrate, 5% DMSO in the presence of 0 µM, 0.1 µM, 1.0 µM and 10 µM of inhibitor, in 96 well plates by measuring absorbance at 405 nm in a plate reader (Spectramax).

Thrombin Assay

Materials: Thrombin (Chromogenics, cat. no. 820712), Substrate S-2288 (Chromogenics, cat. no. 82 08 52)

Thrombin activity was determined at 37° C. in 50 mM Tris, pH 8.3, 130 mM NaCl, with final concentrations of 1 pkat/ml (0.03 µg/ml, 88 pM) of thrombin, 0.5 mM substrate, 5% DMSO in the presence of 0 µM, 0.1 µM, 1.0 µM and 10 µM of inhibitor, in 96 well plates by measuring absorbance at 405 nm in a plate reader (Spectramax).

TABLE 1

Selectivity of substituted 3,1-benzoxazin-4-ones - $IC_{50}$ (µM)

| Compound | | KLK7 | KLK5 | KLK14 | Cathepsin G | Chymotrypsin | Trypsin | Thrombin |
|---|---|---|---|---|---|---|---|---|
| 1 | (structure) | 0.048 | 0.2 | 0.1 | >>10 | >>10 | >>10 | >10 |
| 2 | (structure) | 0.073 | 0.5 | 0.1 | >10 | >>10 | >>10 | >10 |
| 3 | (structure) | 0.116 | 0.6 | 0.5 | 1.1 | >>10 | >>10 | >10 |
| 4 | (structure) | 0.230 | 1.0 | 1.0 | 2.8 | >>10 | >>10 | >10 |

TABLE 1-continued

Selectivity of substituted 3,1-benzoxazin-4-ones - IC$_{50}$ (μM)

| Compound | | KLK7 | KLK5 | KLK14 | Cathepsin G | Chymotrypsin | Trypsin | Thrombin |
|---|---|---|---|---|---|---|---|---|
| 5 | (structure) | 0.085 | 0.5 | 0.3 | 1.2 | >10 | >>10 | >10 |
| 6 | (structure) | 0.080 | 1.0 | 1.4 | 0.7 | <0.1 | >>10 | 0.6 |
| 7 | (structure) | 0.090 | 2.2 | 2.7 | 1.9 | <0.1 | >>10 | 0.5 |
| 8 | (structure) | 0.065 | 1.0 | 2.3 | 0.6 | <0.1 | >>10 | >10 |
| 9 | (structure) | 0.228 | 1.3 | 1.5 | 1.3 | 0.4 | >>10 | 0.9 |
| 10 | (structure) | 0.188 | 1.9 | 5.2 | 0.5 | 0.2 | >>10 | 0.5 |

TABLE 1-continued

Selectivity of substituted 3,1-benzoxazin-4-ones - IC$_{50}$ (μM)

| | Compound | KLK7 | KLK5 | KLK14 | Cathepsin G | Chymotrypsin | Trypsin | Thrombin |
|---|---|---|---|---|---|---|---|---|
| 11 | | 1.370 | >10 | >10 | >>10 | 1.0 | >>10 | >10 |
| 12 | | 0.147 | 1.0 | 1.1 | 0.7 | 0.6 | >>10 | >>10 |
| 13 | | 0.155 | 0.6 | 0.8 | 0.7 | <0.1 | 1.8 | 3.0 |
| 14 | | 0.183 | 0.6 | 1.5 | 0.2 | <0.1 | 1.8 | 3.0 |
| 15 | | 0.105 | 0.5 | 0.5 | 0.5 | <0.1 | 3.7 | 0.6 |
| 16 | | 0.149 | 1.0 | 1.3 | 0.4 | <0.1 | 3.7 | 0.6 |

TABLE 1-continued

Selectivity of substituted 3,1-benzoxazin-4-ones - IC$_{50}$ (μM)

| Compound | | KLK7 | KLK5 | KLK14 | Cathepsin G | Chymotrypsin | Trypsin | Thrombin |
|---|---|---|---|---|---|---|---|---|
| 17 | 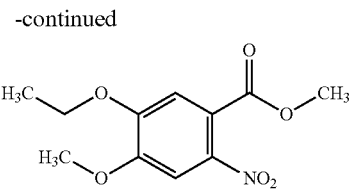 | 0.175 | 1.0 | 1.1 | 0.1 | 1.2 | >>10 | >>10 |
| 18 | 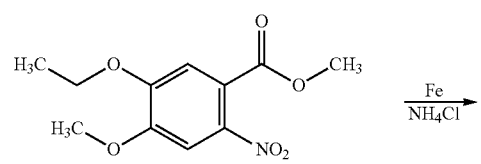 | 0.10 | 4.5 | 2.1 | 1.9 | >10 | >>10 | >10 |

As seen in Table 1 only compound 1 (6-ethoxy-7-methoxy-2-(2-methylsulfanylphenyl)-3,1-benzoxazin-4-one) and compound 2 (2-(2-chlorophenyl)-6-ethoxy-7-methoxy-3,1-benzoxazin-4-one) were found to have the desired selectivity, i.e. an IC$_{50}$ below 0.1 μM for KLK7, an IC$_{50}$ below 1 μM for KLK5 and KLK14, and an IC$_{50}$ above 10 μM for the other proteases tested.

It should be noted that although several compounds were found to have a strong inhibitory effect on KLK7, as well as KLK5 and KLK14, only compounds 1 and 2, i.e. the compounds according to the invention, could be demonstrated to have a sufficiently low inhibitory activity for other proteases.

Even small changes in the substation pattern of the compounds have a dramatic effect on the selectivity of the compounds. For example, compound 12 being methoxy substituted in position 6, as compared to compound 1 being ethoxy substituted in position 6, shows a more than 10 fold higher inhibitory activity (seen as a 10 fold lower IC$_{50}$) on Cathepsin G and Chymotrypsin compared to compound 1, making compound 12 unsuitable for use in the treatment of skin diseases.

In summary, the data presented in Table 1 demonstrates that only compounds 1 and 2, i.e. the compounds according to the invention, are sufficiently selective having a high inhibitory activity for the skin proteases KLK7, KLK5, and KLK14, while having a sufficiently low inhibitory activity for other proteases, making them suitable for use in the treatment of skin diseases.

Example 2

Synthesis of 6-ethoxy-7-methoxy-2-(2-methylsulfanylphenyl)-3,1-benzoxazin-4-one

Step 1

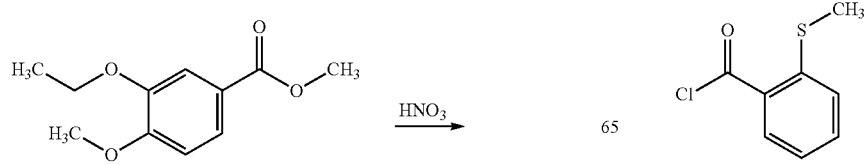

$\xrightarrow{HNO_3}$

-continued

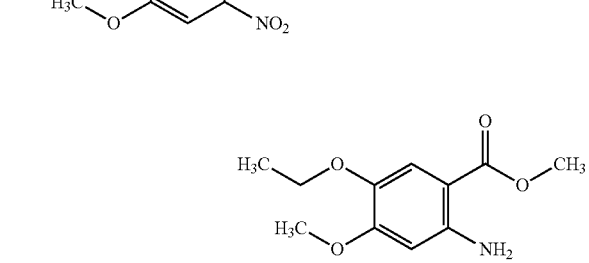

Step 2

$\xrightarrow[NH_4Cl]{Fe}$

Step 3

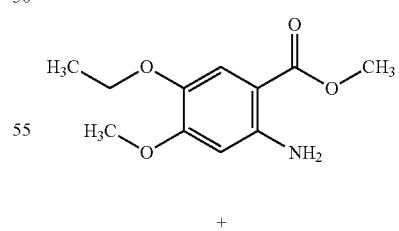

+

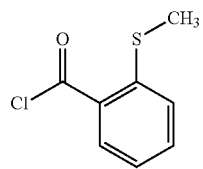

$\xrightarrow{SOCl_2}$

15
-continued

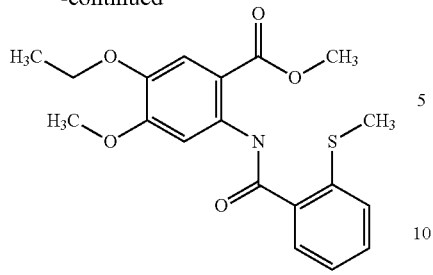

Step 4

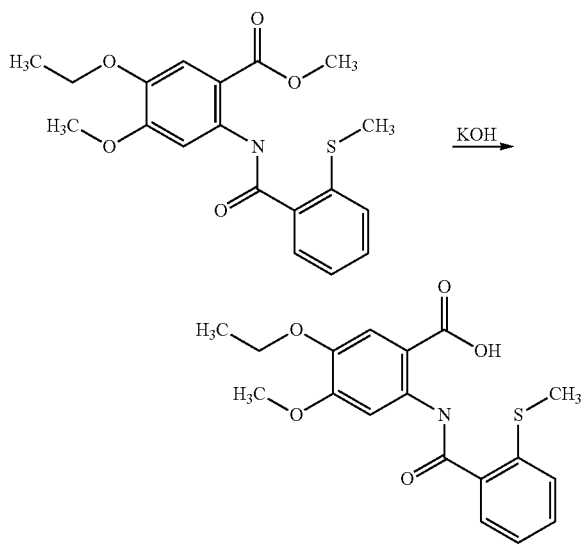

Step 5

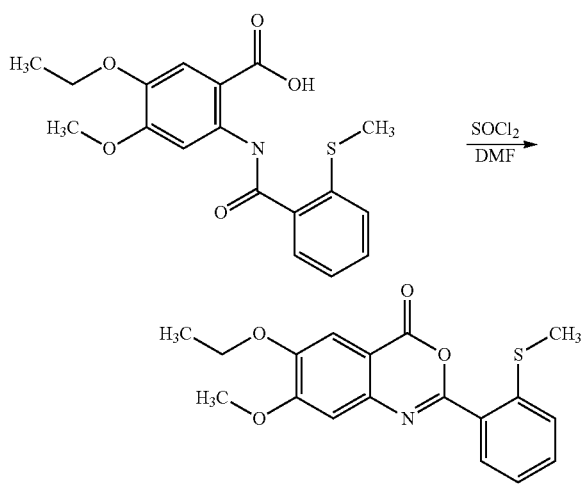

16

Example 3

Synthesis of 2-(2-chlorophenyl)-6-ethoxy-7-methoxy-3,1-benzoxazin-4-one

Same as in Example 2 but with use of

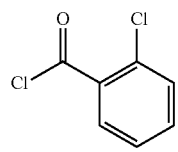

in Step 3.

The invention claimed is:

1. A compound according to Formula I

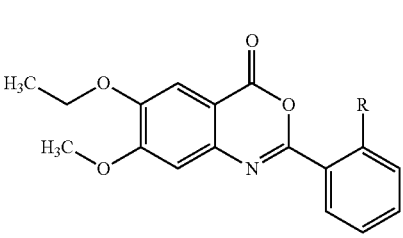

Formula I wherein R is —S—CH$_3$ or —Cl, or a pharmaceutically acceptable salt thereof.

2. The compound 6-Ethoxy-7-methoxy-2-(2-methylsulfanylphenyl)-3,1-benzoxazin-4-one.

3. The compound 2-(2-Chlorophenyl)-6-ethoxy-7-methoxy-3,1-benzoxazin-4-one.

4. A method for treatment of a skin disease selected from Netherton syndrome, atopic dermatitis, contact dermatitis, eczema, psoriasis, acne, epidermal hyperkeratosis, acanthosis, epidermal inflammation, dermal inflammation and pruritus comprising: administrating a therapeutically active amount of a compound according to claim 1, to a subject in need of such treatment.

5. The method according to claim 4, wherein the skin disease is Netherton syndrome.

* * * * *